US012465252B2

(12) United States Patent
Kunardi

(10) Patent No.: US 12,465,252 B2
(45) Date of Patent: Nov. 11, 2025

(54) BLOOD COLLECTION DEVICES, SYSTEMS, AND METHODS

(71) Applicant: Becton, Dickinson and Company, Franklin Lakes, NJ (US)

(72) Inventor: Linda Kunardi, Serangoon (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 621 days.

(21) Appl. No.: 16/532,178

(22) Filed: Aug. 5, 2019

(65) Prior Publication Data

US 2020/0060593 A1 Feb. 27, 2020

Related U.S. Application Data

(60) Provisional application No. 62/722,058, filed on Aug. 23, 2018.

(51) Int. Cl.

| | |
|---|---|
| ***A61B 5/15*** | (2006.01) |
| ***A61B 5/153*** | (2006.01) |
| ***A61M 39/10*** | (2006.01) |

(52) U.S. Cl.

CPC .... *A61B 5/15003* (2013.01); *A61B 5/150351* (2013.01); *A61B 5/150534* (2013.01); *A61B 5/150206* (2013.01); *A61B 5/150473* (2013.01); *A61B 5/153* (2013.01); *A61M 2039/1077* (2013.01); *A61M 2039/1088* (2013.01)

(58) Field of Classification Search

CPC .......... A61B 5/15003; A61B 5/150534; A61B 5/150351; A61B 5/153; A61B 5/150473; A61B 5/150992; A61B 5/150206; A61M 2039/1077; A61M 2039/1088; A61M 5/345; A61M 39/12; A61J 15/0026; B01L 2300/042; B01L 2300/0832; B01L 3/50825; B01L 2300/0858; B01L 2300/043;

(Continued)

(56) References Cited

U.S. PATENT DOCUMENTS 5,202,093 A * 4/1993 Cloyd ................. B01L 3/50825 435/288.1
7,387,216 B1 6/2008 Smith (Continued)

FOREIGN PATENT DOCUMENTS

EP 2380665 10/2011
EP 3042691 7/2016

(Continued)

*Primary Examiner* — Alex M Valvis
*Assistant Examiner* — Chanel J Jhin
(74) *Attorney, Agent, or Firm* — Kirton McConkie; Whitney Blair; Kevin Stinger

(57) ABSTRACT

A blood collection apparatus may include a connector, which may include a distal end, a proximal end, and a lumen extending there between. The distal end may include a male luer lock fitting configured to couple to a proximal end of a catheter adapter, and the proximal end may include a male luer slip fitting. The blood collection apparatus may include a lid, which may include a body, a closure, and a tether connecting the body to the closure. The body may include a cover portion and an inner wall extending from the cover portion. The inner wall may be aligned with an aperture extending through the cover portion. The inner wall and the aperture may form a channel configured to receive the male luer slip fitting.

12 Claims, 7 Drawing Sheets

(58) Field of Classification Search
CPC .. B65D 43/02; B65D 25/005; B65D 2251/00; B65D 83/0481
USPC .......................................................... 600/576
See application file for complete search history.

(56) References Cited

U.S. PATENT DOCUMENTS

| | | | | |
|---|---|---|---|---|
| 8,383,044 | B2 * | 2/2013 | Davis | A61B 5/150267 600/580 |
| 2006/0037903 | A1 | 2/2006 | Smith et al. | |
| 2009/0308184 | A1 * | 12/2009 | Blekher | A61B 5/150274 220/254.1 |
| 2010/0176584 | A1 * | 7/2010 | Ito | A61M 39/10 285/23 |
| 2016/0073937 | A1 * | 3/2016 | Burkholz | A61B 5/150251 604/524 |
| 2016/0129235 | A1 | 5/2016 | Ryan | |
| 2016/0206516 | A1 * | 7/2016 | Kunishige | A61J 15/00 |
| 2017/0014310 | A1 | 1/2017 | Hyun et al. | |

FOREIGN PATENT DOCUMENTS

| | | | |
|---|---|---|---|
| EP | 3840649 | B1 | 6/2023 |
| JP | 2015051092 | A | 3/2015 |
| WO | 2011/071897 | | 6/2011 |
| WO | 2011/073729 | | 6/2011 |

* cited by examiner

BLOOD COLLECTION DEVICES, SYSTEMS, AND METHODS

RELATED APPLICATIONS

This application claims the benefit of U.S. Provisional Patent Application No. 62/722,058, filed on Aug. 23, 2018, entitled "BLOOD COLLECTION DEVICES, SYSTEMS, AND METHODS," which is incorporated herein in its entirety.

BACKGROUND

A VACUTAINER™ blood collection tube may include a sterile glass or plastic test tube with a rubber stopper that creates a vacuum inside of the tube, facilitating the drawing of a predetermined volume of blood from a patient. In order to draw blood from the patient, a double-ended needle may be used. A proximal end of the needle may be positioned inside a holder, and a distal end of the needle may be inserted into a vein of a patient. When the VACUTAINER™ blood collection tube is inserted into the holder, the rubber stopper may be punctured by the proximal end of the needle, and the vacuum in the tube may pull blood through the needle into the tube. The filled tube may then be removed and another tube can be inserted and filled the same way.

This method of drawing blood can be expensive due to the cost of the needle, which is metal, as well as the rubber stopper. Furthermore, the needle may pose a hazard to clinicians. Clinicians in some markets, due to cost and other factors, may not use the VACUTAINER™ approach, and may resort to more dangerous practices that increase a risk of blood exposure. There is a need for blood collection systems and methods that are safe and cost-effective.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a blood collection apparatus and related methods. In some embodiments, the blood collection apparatus may include a connector. In some embodiments, the connector may include a distal end, a proximal end, and a lumen extending there between. In some embodiments, the distal end may include a male luer lock fitting configured to couple to a proximal end of a catheter adapter, which may include a female luer fitting. In some embodiments, the proximal end of the connector may include a male luer slip fitting.

In some embodiments, the blood collection apparatus may include a lid for a blood collection tube. In some embodiments, the lid may include a body, which may include a cover portion and an inner wall extending from the cover portion. In some embodiments, the inner wall may be aligned with an aperture extending through the cover portion. In some embodiments, the inner wall and the aperture may form a channel configured to receive the male luer slip fitting of the connector. In some embodiments, the inner wall may be tapered to receive the male luer slip fitting of the connector.

In some embodiments, the lid may include a closure and/or a tether connecting the body to the closure. In some embodiments, the closure may include an annular flange, which may fit inside and contact a circumference of the channel when the closure is in a closed position. In some embodiments, the annular flange may include an outer circumference less than a circumference of the channel. In some embodiments, the annular flange may include an outer circumference larger than a circumference of the channel or approximately a same size as the circumference of the channel.

In some embodiments, the body of the lid may include a generally cylindrical outer wall. In some embodiments, the closure may include another annular flange, which may contact the outer circumference of the outer wall when the closure is in a closed position. In some embodiments, the other annular flange may include an inner circumference greater than the outer circumference of the outer wall. In some embodiments, the other annular flange may include an inner circumference less than or approximately equal to the outer circumference of the outer wall.

In some embodiments, an outer surface of the cover portion may be generally planar. In some embodiments, an inner surface of the cover portion disposed between the inner wall and the outer wall is generally planar.

In some embodiments, the blood collection apparatus may include the blood collection tube coupled to the lid. In some embodiments, the blood collection tube may include a rim forming an opening into a cavity of the blood collection tube. In some embodiments, the inner wall may extend through the opening. In some embodiments, the rim may contact an inner surface of the outer wall of the body. In some embodiments, the inner surface of the outer wall may include one or more grooves, which may extend generally parallel to a central axis of the lid. In some embodiments, the grooves may be permeable to air but not blood.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
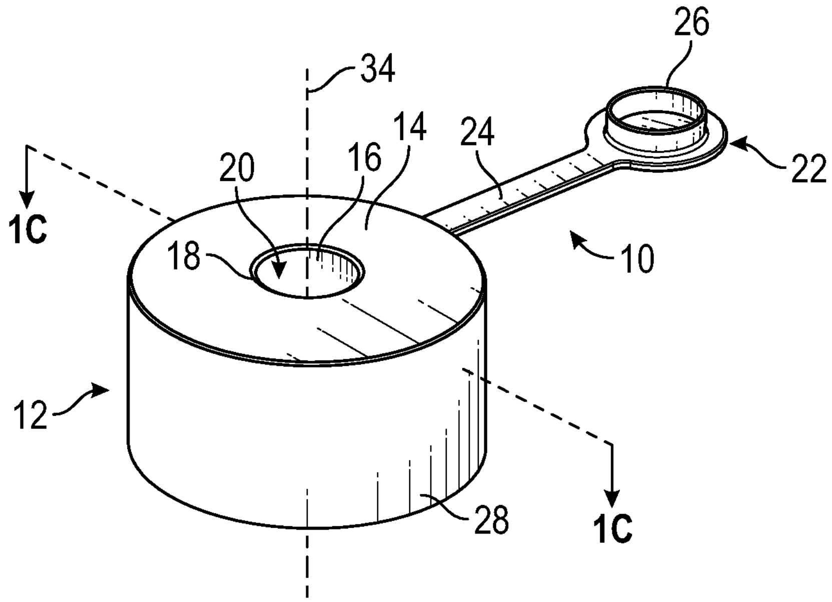
FIG. 1A is an upper perspective view of an example lid, according to some embodiments.
Figure 1B:
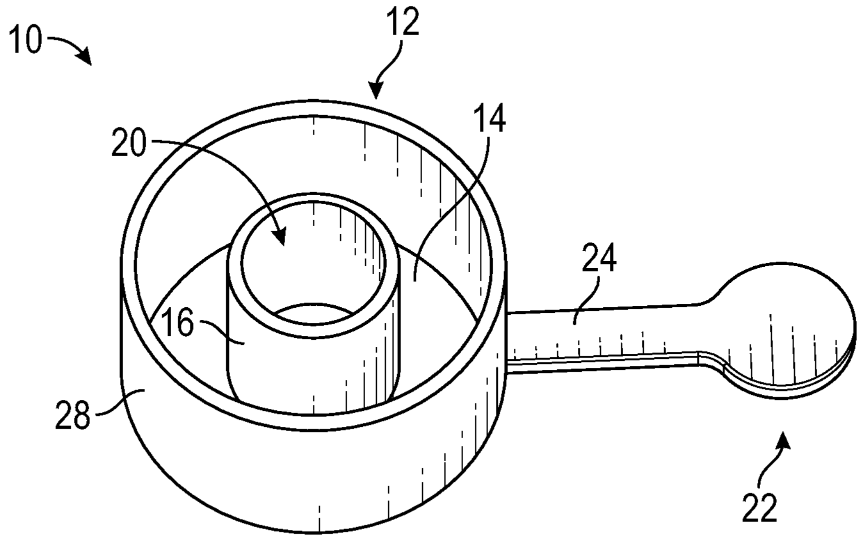
FIG. 1B is a lower perspective view of the lid of FIG. 1A, according to some embodiments.

Referring now to FIGS. 1A-1D, in some embodiments, a lid 10 for a blood collection tube may include a body 12, which may include a cover portion 14 and an inner wall 16 extending from the cover portion 14. In some embodiments, the inner wall 16 may be aligned with an aperture 18 extending through the cover portion 14. In some embodiments, the inner wall 16 and the aperture 18 may form a channel 20, which may be configured to receive a male luer slip fitting of a connector. In some embodiments, the inner wall 16 may be tapered to receive the male luer slip fitting of the connector. In some embodiments, the inner wall 16 may not be tapered.

In some embodiments, the lid 10 may include a closure 22 and/or a tether 24 connecting the body 12 to the closure 22. In some embodiments, the closure 22 may include an annular flange 26, which may fit inside and contact a circumference of the channel 20 when the closure 22 is in a closed position, as illustrated, for example, in FIG. 2D. In some embodiments, the annular flange 26 may include an outer circumference less than a circumference of the channel 20. In some embodiments, the annular flange 26 may include an outer circumference larger than a circumference of the channel 20 or approximately a same size as the circumference of the channel 20 such that the annular flange 26 is secured within the channel 20 in an interference fit.

In some embodiments, the body 12 of the lid 10 may include a generally cylindrical outer wall 28. In some embodiments, the tether 24 may extend from the outer wall 28 and/or the cover portion 14. In some embodiments, an outer surface of the cover portion 14 may be generally planar. In some embodiments, an inner surface of the cover portion disposed between the inner wall 16 and the outer wall 28 may be generally planar.

Figure 1C:
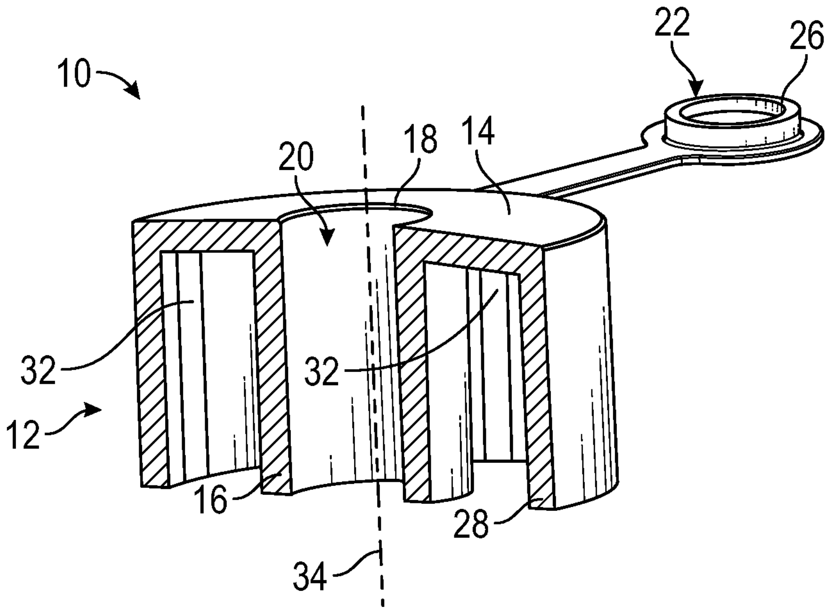
FIG. 1C is a cross-sectional view of the lid of FIG. 1A along the line 1C-1C of FIG. 1A, according to some embodiments.
Figure 1D:
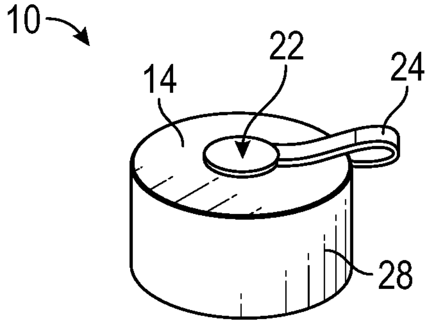
FIG. 1D is an upper perspective view of the lid of FIG. 1A in a closed position, according to some embodiments.

As illustrated in FIG. 1C, in some embodiments, the inner surface of the outer wall 28 may include one or more grooves 32, which may extend generally parallel to a central axis 34 of the lid 10. In some embodiments, the grooves 32 may act as vents and have dimensions such that the grooves 32 are permeable to air but not blood.

Figure 4:
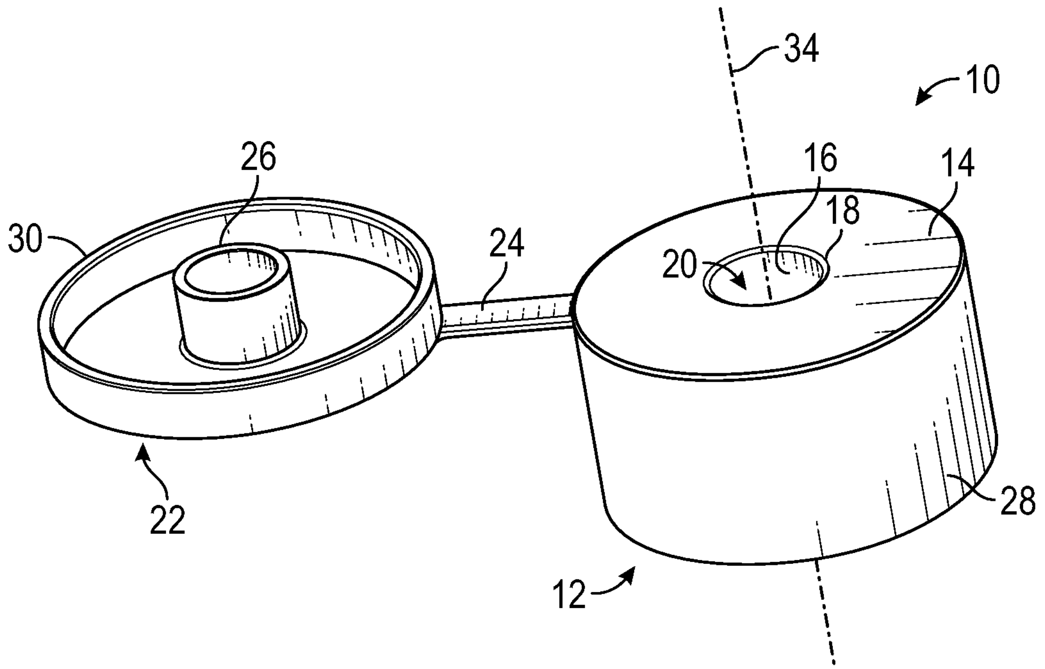
FIG. 4 is an upper perspective view of the lid of FIG. 1A having a second annular flange, according to some embodiments.

Referring now to FIG. 4, in some embodiments, the closure 22 of the lid 10 may include another annular flange 30, which may contact the outer circumference of the outer wall 28 when the closure 22 is in a closed position. In some embodiments, the other annular flange 30 may include an inner circumference greater than the outer circumference of the outer wall 28. In some embodiments, the other annular flange 30 may include an inner circumference less than or approximately equal to the outer circumference of the outer wall.

Figure 2A:
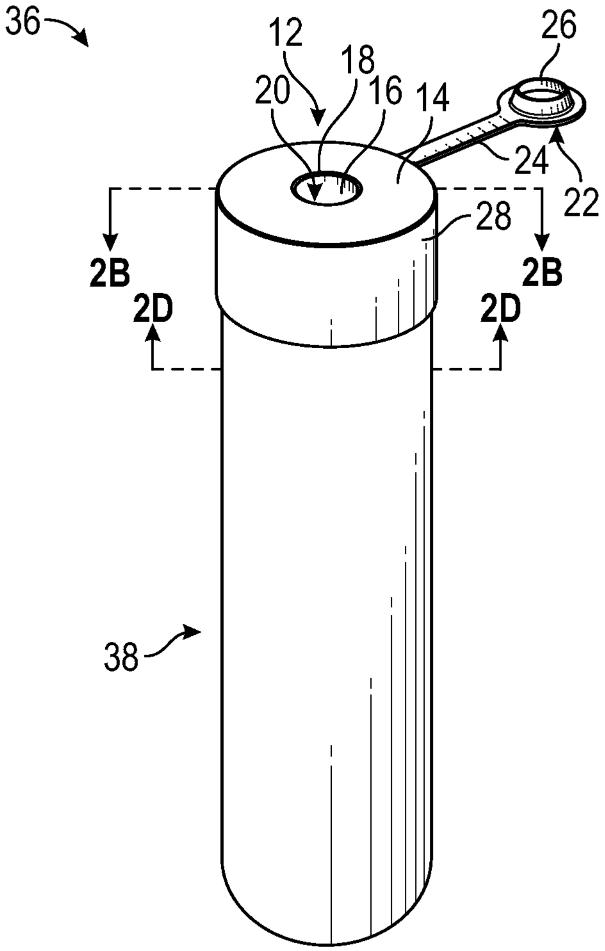
FIG. 2A is an upper perspective view of the lid of FIG. 1A coupled to an example blood collection tube, illustrating an example closure of the lid in an open position, according to some embodiments.
Figure 2B:
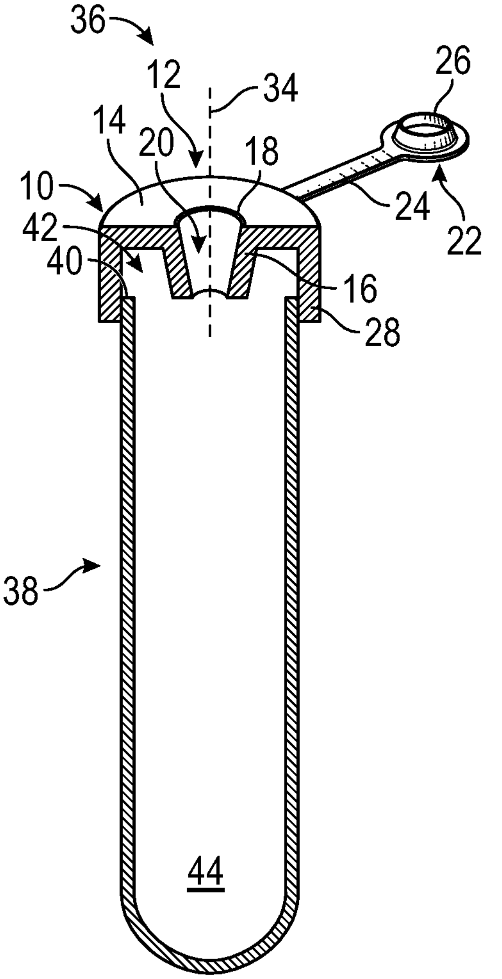
FIG. 2B is a cross-sectional view of the lid and the blood collection tube of FIG. 2A along the line 2B-2B of FIG. 2A, according to some embodiments.
Figure 2C:
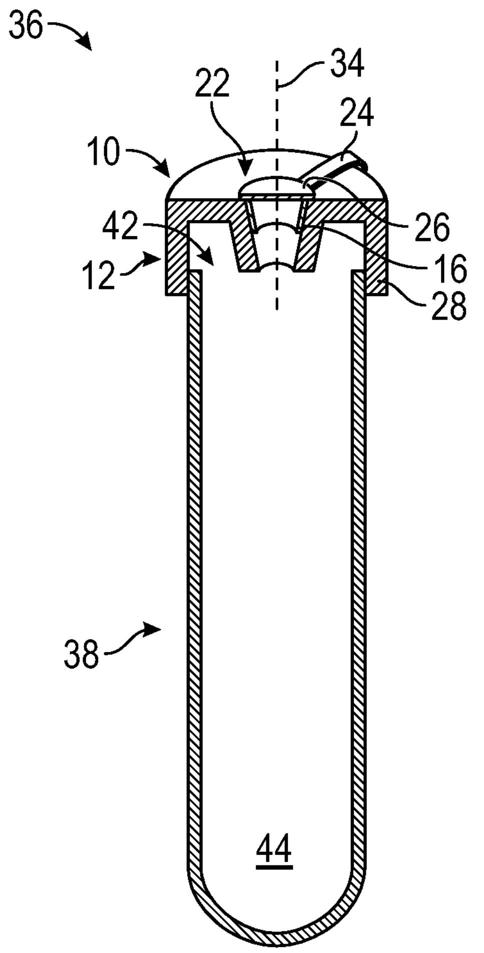
FIG. 2C is a cross-sectional view of the lid and the blood collection tube of FIG. 2A along the line 2B-2B of FIG. 2A, illustrating the closure in a closed position, according to some embodiments.

Referring now to FIGS. 2A-2D, in some embodiments, a blood collection apparatus 36 may include the lid 10 and/or a blood collection tube 38. In some embodiments, the blood collection tube 38 may be coupled to the lid 10. In some embodiments, the blood collection tube 38 may include a rim 40 forming an opening 42 into a cavity 44 of the blood collection tube 38. In some embodiments, the rim 40 may be annular. In some embodiments, the inner wall 16 of the lid 10 may extend a same distance as the outer wall 28, as illustrated in FIG. 1C, for example, or a different distance, as illustrated in FIG. 2B-2C, for example.

Figure 2D:
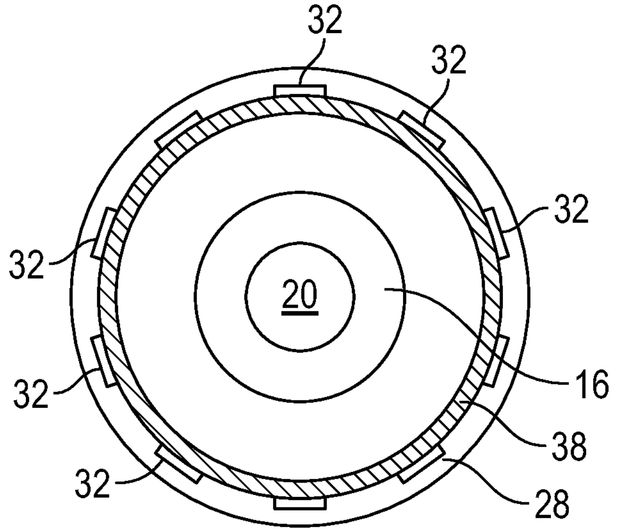
FIG. 2D is a cross-sectional view of the lid and the blood collection tube of FIG. 2A along the line 2D-2D of FIG. 2A, according to some embodiments.

In some embodiments, the inner wall 16 of the body 12 may extend through the opening 42. In some embodiments, the rim 40 may contact the inner surface of the outer wall 28 of the body 12. FIG. 2D illustrates the grooves 32, which may be generally parallel to the central axis of the lid, according to some embodiments. In some embodiments, air may pass between an exterior of the blood collection apparatus 36 and the cavity 44 of the blood collection tube 38 via the grooves 32, but the grooves 32 may be impermeable to blood to prevent leakage of blood from the cavity 44.

FIGS. 2C illustrates the lid 10 in a closed position, according to some embodiments. In some embodiments, the annular flange 26 may fit inside and contact a circumference of the channel 20 when the lid 10 is in the closed position. For example, the annular flange 26 may fit inside and contact a circumference of the aperture 18 and/or a circumference of the inner wall 16.

Figure 3A:
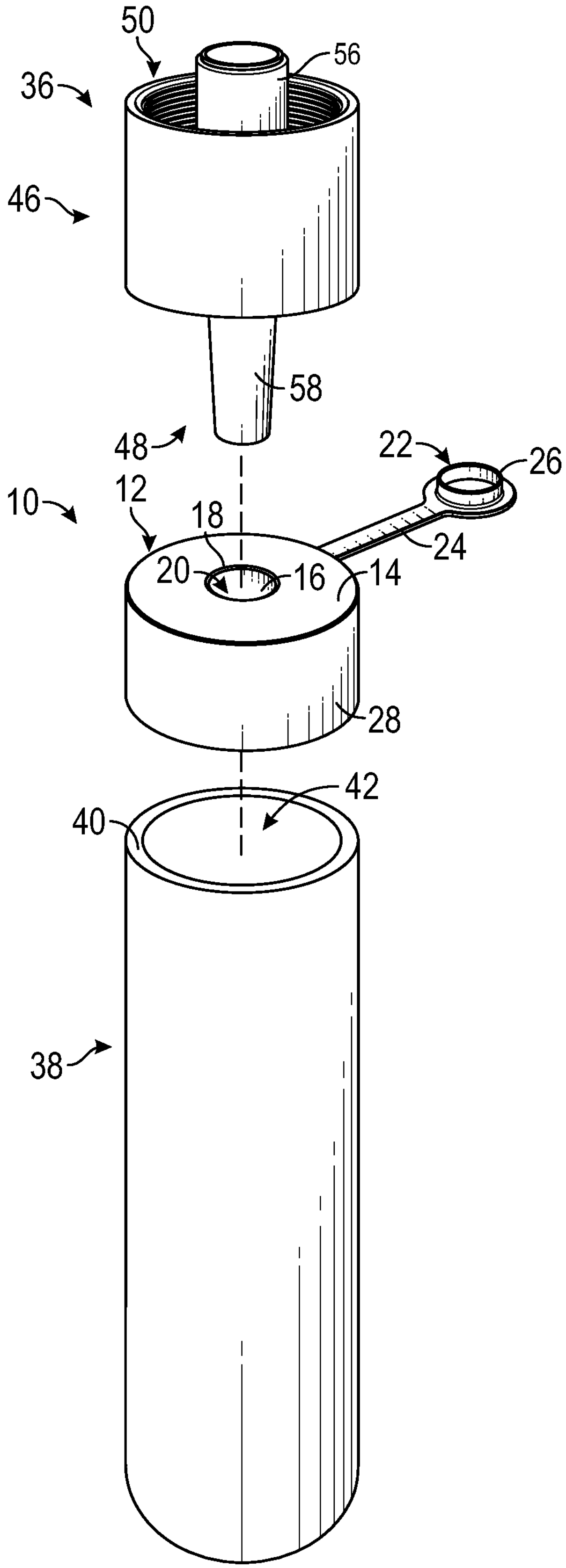
FIG. 3A is an exploded view of an example blood collection apparatus, according to some embodiments.
Figure 3B:
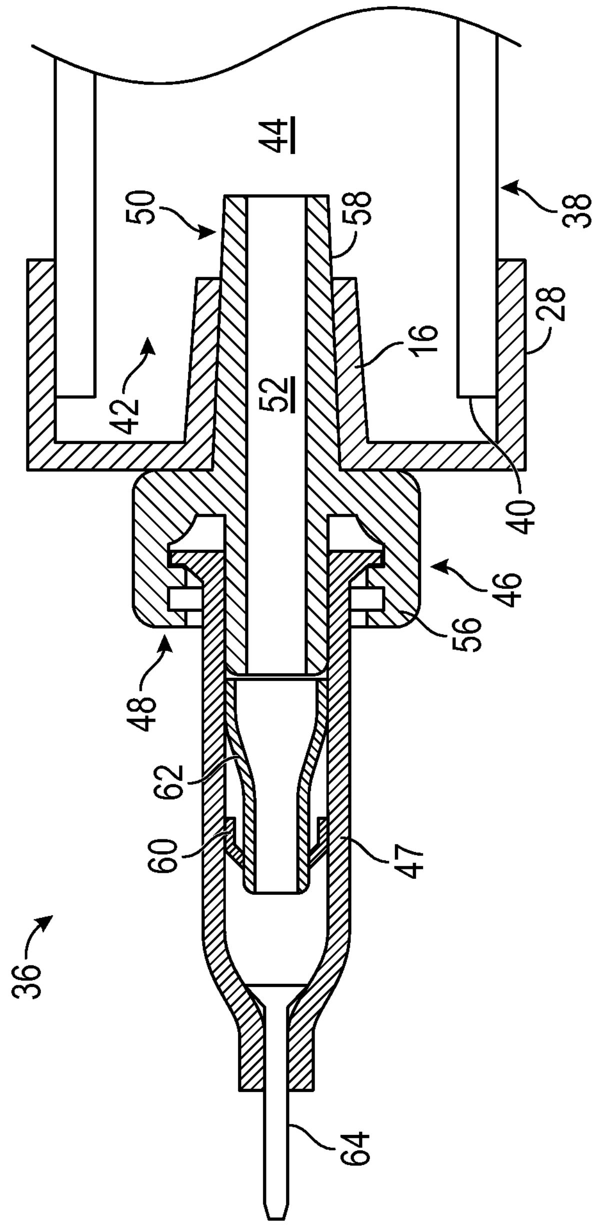
FIG. 3B is a cross-sectional view illustrating the lid of FIG. 1A, an example connector, and an example catheter adapter coupled together, according to some embodiments.

Referring now to FIGS. 3A-3B, in some embodiments, the blood collection apparatus 36 may include the connector 46 and/or a catheter adapter 47. In some embodiments, the connector 46 may include a distal end 48, a proximal end 50, and a lumen 52 extending there between. In some embodiments, the distal end 48 may include a male luer lock fitting 56 configured to couple to a proximal end of the catheter adapter 47, as illustrated, for example, in FIG. 3B. In some embodiments, the proximal end of the catheter adapter 47 may include a female luer fitting. In some embodiments, the proximal end 50 may include a male luer slip fitting 58.

In some embodiments, the male luer lock fitting 56 may form a seal with the catheter adapter 47 or another medical device, preventing fluid leakage. In some embodiments, the male luer slip fitting 58 may seal the lid 10 when the male luer slip fitting 58 is inserted into the channel 20. In some embodiments, the male luer lock fitting 56 may include threading, which may form a sealed connection with the catheter adapter 47. In some embodiments, the male luer slip fitting 58 may act as a funnel, allowing blood to be channeled into the blood collection tube 38, while reducing or eliminating blood spill or splash.

In some embodiments, the catheter adapter 47 may include any catheter adapter known in the art. In some embodiments, the catheter adapter 47 may include a septum 60 and/or septum actuator 62. In other embodiments, the male luer lock fitting 56 may act as a septum actuator. In some embodiments, a catheter 64 may extend distally from a distal end of the catheter adapter 47. In some embodiments, the catheter 64 may include a peripheral intravenous catheter.

In some embodiments, the catheter 64 and the catheter adapter 47 may be used for a variety of infusion therapies. For example, the catheter 64 and the catheter adapter 47 may be used for infusing fluids, such as normal saline solution, various medicaments, and total parenteral nutrition, into a patient. In some embodiments, the catheter 64 and the catheter adapter 47 may also be used for withdrawing blood from the patient.

In some embodiments, the catheter 64 may include an over-the-needle peripheral intravenous catheter ("PIVC"), which may be mounted over an introducer needle having a sharp distal tip (not illustrated). In some embodiments, the catheter 64 and the introducer needle may be assembled so that the distal tip of the introducer needle extends beyond the distal tip of the catheter 64 with the bevel of the needle facing up away from skin of the patient. In some embodiments, the catheter 64 and introducer needle may be inserted at a shallow angle through the skin into vasculature of the patient.

In order to verify proper placement of the introducer needle and/or the catheter 64 in the vein, a user generally confirms that there is "flashback" of blood. Once placement of the needle has been confirmed, a user may temporarily occlude flow in the vein and remove the introducer needle, leaving the catheter 64 in place within the vein. In some embodiments, after the catheter 64 is placed within the vein and the introducer needle withdrawn, the lid 10 may be coupled to the catheter adapter 47 and blood may be collected in the blood collection tube 38.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A blood collection apparatus, comprising:
- a blood collection tube comprising an open distal end, a closed proximal end, and a cavity extending between the open distal end and the closed proximal end;
- a connector comprising a distal end, a proximal end, and a lumen extending there between, wherein the distal end comprises a male luer lock fitting configured to couple to a proximal end of a catheter adapter, and wherein the proximal end of the connector comprises a male luer slip fitting; and
- a lid coupled to the open distal end of the blood collection tube, wherein the lid comprises:
- a body having a cylindrical outer wall, a cover portion and an inner wall extending from the cover portion, wherein the inner wall is aligned with an aperture extending through the cover portion, wherein the inner wall and the aperture form a channel, wherein the male luer slip fitting is secured in the channel and extends through the channel into the blood collection tube, wherein an inner surface of the cylindrical outer wall comprises a plurality of grooves extending parallel to a central axis of the lid, wherein air passes between an exterior of the blood collection apparatus and the cavity of the blood collection tube via the plurality of grooves, wherein the grooves are impermeable to blood to prevent leakage of blood from the cavity;
- a closure, wherein the closure comprises an annular flange that fits inside and contacts a circumference of the channel when the closure is in a closed position, and wherein the closure further comprises another annular flange, wherein the other annular flange contacts an outer circumference of the cylindrical outer wall when the closure is in the closed position; and
- a tether connecting the body to the closure.

2. The blood collection apparatus of claim 1, wherein the annular flange comprises an outer circumference less than the circumference of the channel.

3. The blood collection apparatus of claim 1, wherein the annular flange comprises an outer circumference larger than the circumference of the channel or approximately a same size as the circumference of the channel.

4. The blood collection apparatus of claim 1, wherein the other annular flange comprises an inner circumference greater than the outer circumference of the cylindrical outer wall.

5. The blood collection apparatus of claim 1, wherein the other annular flange comprises an inner circumference less than or approximately equal to the outer circumference of the cylindrical outer wall.

6. The blood collection apparatus of claim 1, wherein the inner wall is tapered to receive the male luer slip fitting.

7. The blood collection apparatus of claim 1, wherein an outer surface of the cover portion is planar.

8. The blood collection apparatus of claim 1, wherein an inner surface of the cover portion disposed between the inner wall and the cylindrical outer wall is planar.

9. The blood collection apparatus of claim 1, wherein the blood collection tube comprises a rim forming an opening into a cavity of the blood collection tube, wherein the inner wall extends through the opening, wherein the rim contacts the inner surface of the cylindrical outer wall of the body.

10. A blood collection apparatus, comprising:
- a blood collection tube comprising an open distal end, a closed proximal end, and a cavity extending between the open distal end and the closed proximal end;
- a connector comprising a distal end, a proximal end, and a lumen extending there between, wherein the distal end comprises a male luer lock fitting configured to couple to a proximal end of a catheter adapter, wherein the proximal end of the connector comprises a male luer slip fitting, wherein the male luer slip fitting is a funnel, allowing blood to be channeled into the blood collection tube;
- a lid coupled to the open distal end of the blood collection tube and coupled to the connector, wherein the lid comprises:
- a body having a cylindrical outer wall, a cover portion and an inner wall extending from the cover portion, the inner wall aligned with an aperture extending through the cover portion, the inner wall forming a channel, wherein an inner surface of the cylindrical outer wall comprises a plurality of grooves extending parallel to a central axis of the lid, wherein air passes between an exterior of the blood collection apparatus and the cavity of the blood collection tube via the plurality of grooves, wherein the grooves are impermeable to blood to prevent leakage of blood from the cavity;

a closure; and a tether connecting the body to the closure, wherein the closure comprises an annular flange that fits inside and contacts a circumference of the channel when the closure is in a closed position, and the closure further comprises another annular flange that contacts an outer circumference of the cylindrical outer wall when closure is in the closed position.

11. The blood collection apparatus of claim 10, wherein the inner wall is tapered.

12. The blood collection apparatus of claim 10, wherein the blood collection tube comprises a rim forming an opening into the cavity of the blood collection tube, wherein the inner wall extends through the opening, wherein the rim contacts the inner surface of the cylindrical outer wall of the body.

* * * * *